(12) United States Patent
Baert et al.

(10) Patent No.: US 11,395,867 B2
(45) Date of Patent: Jul. 26, 2022

(54) DEGRADABLE REMOVABLE IMPLANT FOR THE SUSTAINED RELEASE OF AN ACTIVE COMPOUND

(71) Applicant: Janssen Sciences Ireland Unlimited Company, County Cork (IE)

(72) Inventors: Lieven Elvire Colette Baert, Bruges (BE); Iksoo Chun, Princeton, NJ (US); Guenter Kraus, Sint-Katelijne-Waver (BE); Deborah M. Schachter, Edison, NJ (US); Qiang Zhang, Annandale, NJ (US)

(73) Assignee: Janssen Sciences Ireland Unlimited Company, County Cork (IE)

( * ) Notice: Subject to any disclaimer, the term of this patent is extended or adjusted under 35 U.S.C. 154(b) by 0 days.

(21) Appl. No.: 16/917,269

(22) Filed: Jun. 30, 2020

(65) Prior Publication Data
US 2020/0330654 A1   Oct. 22, 2020

Related U.S. Application Data

(62) Division of application No. 14/300,607, filed on Jun. 10, 2014, now Pat. No. 10,744,235, which is a division of application No. 13/515,380, filed as application No. PCT/EP2010/070246 on Dec. 20, 2010, now Pat. No. 8,784,858.

(60) Provisional application No. 61/288,373, filed on Dec. 21, 2009.

(51) Int. Cl.
| | |
|---|---|
| A61L 31/14 | (2006.01) |
| A61K 9/50 | (2006.01) |
| A61K 9/00 | (2006.01) |
| A61K 45/06 | (2006.01) |
| A61K 31/505 | (2006.01) |
| A61K 31/343 | (2006.01) |
| A61K 31/34 | (2006.01) |
| A61K 9/14 | (2006.01) |
| A61K 9/06 | (2006.01) |

(52) U.S. Cl.
CPC .......... *A61L 31/148* (2013.01); *A61K 9/0024* (2013.01); *A61K 9/0092* (2013.01); *A61K 9/14* (2013.01); *A61K 9/5031* (2013.01); *A61K 31/34* (2013.01); *A61K 31/343* (2013.01); *A61K 31/505* (2013.01); *A61K 45/06* (2013.01); *A61L 31/146* (2013.01); *A61K 9/06* (2013.01); *A61K 9/5084* (2013.01)

(58) Field of Classification Search
CPC ............. A61K 9/0024; A61K 2300/00; A61K 9/0092; A61K 35/22; A61K 35/30; A61K 38/185; A61K 9/0004; A61K 9/0051; A61K 38/29; A61K 9/0097; A61K 9/2072; A61K 2039/515; A61K 51/1282; A61K 9/0085; A61K 9/1273; A61K 9/1635; A61K 9/1652; A61K 9/2886; A61K 51/1241; A61K 9/0009; A61K 9/0036; A61K 9/2095; A61K 9/703; A61K 9/7038; A61M 2210/0687; A61M 2230/005; A61M 2210/0693; A61M 31/002; A61P 31/18; A61P 31/00; A61P 31/12; A61P 33/06; A61P 37/00; A61P 37/02; A61P 37/04; A61P 43/00; A61F 13/02; A61F 2013/00157; A61F 2013/00229; A61F 2013/00574; A61F 2013/00625; A61F 2013/00638; A61F 2013/0068; A61F 2013/00748; A61F 2013/00876; A61F 2013/00906; A61F 2013/0091; A61F 2/022; A61F 13/0276; A61F 2013/00817; A61F 2013/0296; A61F 2250/0068; A61L 24/04; A61L 24/08; A61L 26/0009; A61L 26/0023; A61L 27/3804; A61L 2300/45; A61L 27/54; A61L 27/56; A61L 31/146; A61L 31/16
See application file for complete search history.

(56) References Cited

U.S. PATENT DOCUMENTS

| | | | |
|---|---|---|---|
| 5,182,111 | A | 1/1993 | Aebischer et al. |
| 5,705,270 | A | 1/1998 | Soon-Shiong et al. |
| 7,261,529 | B2 | 8/2007 | Persyn et al. |
| 2001/0026804 | A1 | 10/2001 | Boutignon |
| 2004/0082937 | A1 | 4/2004 | Ausiello et al. |
| 2004/0086517 | A1 | 5/2004 | TenHuisen et al. |

(Continued)

FOREIGN PATENT DOCUMENTS

| | | |
|---|---|---|
| EP | 1454641 A2 | 9/2004 |
| JP | 512250/97 | 12/1997 |

(Continued)

OTHER PUBLICATIONS

Goraltchouk et al., "Incorporation of protein-eluting microspheres into biodegradable nerve guidance channels for controlled release", Journal of Controlled Release 110 (2006) pp. 400-407.

(Continued)

*Primary Examiner* — Audrea B Coniglio
(74) *Attorney, Agent, or Firm* — Sofia Kopelevich

(57) ABSTRACT

A degradable, removable, pharmaceutical implant for the sustained release of one or more drugs in a subject, wherein the pharmaceutical implant is composed of a tube comprising an outer wall made of a degradable polymer completely surrounding a cavity, wherein the outer wall has a plurality of openings and wherein the cavity contains one or more sets of micro-particles, which micro-particles contain an active agent or a combination of two or more active agents, and wherein the size of the microparticles is selected such that the majority of the microparticles cannot pass through the openings.

19 Claims, 5 Drawing Sheets

(56) References Cited

U.S. PATENT DOCUMENTS

| | | |
|---|---|---|
| 2004/0115268 A1 | 6/2004 | Ashton et al. |
| 2006/0252049 A1 | 11/2006 | Shuler et al. |
| 2006/0269475 A1 | 11/2006 | Ryu et al. |
| 2008/0081064 A1 | 4/2008 | Jelle et al. |
| 2009/0036357 A1 | 2/2009 | Harbeson |
| 2011/0257111 A1 | 10/2011 | Harbeson et al. |

FOREIGN PATENT DOCUMENTS

| | | |
|---|---|---|
| JP | 2006-525446 | 11/2006 |
| WO | WO 1995/024261 A1 | 9/1995 |
| WO | WO 1995/024472 A1 | 9/1995 |
| WO | WO 1995/024736 A1 | 9/1995 |
| WO | WO 1996/041368 A1 | 12/1996 |
| WO | WO 1997/047370 A1 | 12/1997 |
| WO | WO 2001/010421 A1 | 2/2001 |
| WO | WO 2001/025240 A1 | 4/2001 |
| WO | WO 2002/30482 A1 | 4/2002 |
| WO | WO 2004/098503 A1 | 11/2004 |
| WO | WO 2005/021001 A1 | 3/2005 |
| WO | WO 2006/106103 A2 | 10/2006 |
| WO | WO 2007/082922 A1 | 7/2007 |
| WO | WO 2009/046299 A2 | 4/2009 |
| WO | WO 2010/072844 A1 | 7/2010 |

OTHER PUBLICATIONS

Gulick, R.M., "New Antiretroviral Drugs", Clinical Microbiology and Infection, (2003), vol. 9, pp. 186-193, Wiley-Blackwell Publishing Ltd.

International Search report and Written Opinion for Application No. PCT/EP2010/070246 dated Dec. 19, 2011.

Porjazoska et al. "Poly(lactide-co-glycolide) microparticles as systems for controlled release of proteins—Preparation and characterization", Acta Pharm. 54, 2004, 215-229.

DEGRADABLE REMOVABLE IMPLANT FOR THE SUSTAINED RELEASE OF AN ACTIVE COMPOUND

CROSS-REFERENCE TO RELATED APPLICATIONS

This application is a divisional of U.S. application Ser. No. 14/300,607, filed 10 Jun. 2014, which is a divisional of U.S. application Ser. No. 13/515,380, filed 12 Jun. 2012, now granted U.S. Pat. No. 8,784,858, which is a national stage application of International Application Number PCT/EP2010/070246, filed 20 Dec. 2010, which claims the benefit of U.S. Provisional Application No. 61/288,373, filed 21 Dec. 2009. The entire content of each of the aforementioned applications is incorporated herein by reference in their entirety.

FIELD OF THE INVENTION

The present invention relates to an implantable depot polymeric device that is easily introduced into the subcutaneous space, removed if the necessity arises, and degrades when drug delivery function is complete. One or multiple drugs can be incorporated. The device introduces a degree of flexibility where the loading of the drug and polymer properties selected for the matrix can be individually tailored for the drug to meet the specific needs of the patient.

BACKGROUND OF THE INVENTION

Implantable drug delivery devices have been known in the art. The device is surgically implanted in the body of a human or veterinary patient and the drug is released in an efficacious manner. Such implantable drug delivery systems are particularly useful for delivering drugs at sustained rates over extended periods of time. Examples of drug delivery implants of this type include Norplant®, Lupron Depot®, and Gliadel Wafer®.

In the art-known implantable drug delivery systems the active ingredient is embedded in a matrix material that is shaped in a cylindrical form of sufficient small size to allow subcutaneous implantation via a hollow needle. A disadvantage associated with such delivery systems is that there is a lag time between implantation and delivery of the drug because the bodily fluids have to penetrate the implant and start decomposing the polymeric matrix. This also often leads to irregularities in the release pattern.

Moreover, none such system has been designed to deliver two or more drugs simultaneously. The utility of an implantable drug delivery system would be increased dramatically when this would be made available. Oftentimes a disease state is more efficaciously addressed when treatment includes two or more active agents that can act together in a more comprehensive, synergistic, or more complimentary fashion. An example of this would be the treatment or prevention of infection where members of two different classes of anti-biotics are released from a single depot system. The activity of each anti-biotic targets different bacterial strains and in this fashion provides for a more comprehensive therapy. Another example of utility would be in the delivery of pain drugs. The sustained release of pain medication can provide for long pain-free periods of time for the patient, which is a significant improvement over the peaks and valleys plasma concentrations of the drug inherent in oral therapy. However, the sustained release of multiple pain drugs that have separate mechanisms of action can result in significantly enhanced pain management.

An even more compelling example for a multi-drug depot can be found in the treatment of infectious diseases, for example HIV (Human Immunodeficiency Virus) and HBV (Hepatitis B Virus). Standard therapy for HIV requires a "cocktail" of at least three drugs. Sustained release therapy for HIV can significantly contribute to therapy compliance (reducing pill burden) and reduce the risk of development of resistance to therapeutic actives. The value for this therapy would increase further if the implantable sustained release formulation contained all the components of the drug cocktail rather than have one sustained release and the others remain as an oral therapy. Other infectious diseases that would benefit from this type of therapy are malaria, flu, TB, and Hepatitis C. A multi-drug depot could also be used in a pre-exposure setting for high risk populations, for instance pre-exposure prophylaxis for HIV infection.

De-coupling the formulation of the two actives into separate processes can substantially improve stability, increase the drug loading of each, and introduces compositionally flexibility where one drug can be formulated to release faster or slower or one drug is increased or decreased in dosage depending on the status of the patient.

The ability to remove the device after implantation is important since many of the drugs used in the sustained release applications are potent and can cause severe even life-threatening reactions. Even compressing the microparticles or pellets together into one unit as described in US 2001/0026804 does not guarantee that the device is removable since once the device is in contact with physiological medium the pellets or microparticles will soon separate from one another making it impossible to completely remove.

US2004/0082937 describes an implantable device for the controlled release of a hormone. The device comprises a substrate with a plurality of reservoirs that each contain a release system that is electrically controllable. US2006/0269475 describes a polymer multi-layer structure having a predetermined micro-fabricated special pattern comprising predetermined reservoirs and channels containing the drug. The polymer multi-layer structure is biodegradable but has a longer lifetime than the duration of the therapy that is delivered. The geometrical pattern of the polymer structure controls the delivery of the therapy while persisting during delivery of the therapy. The device is prepared in layers that are fused together at elevated temperature, which can cause significant warping of the reservoir shape leading to significant changes in the overall loading of the drug in the device or release rate of the drug. Moreover, this void or channel approach to loading the device with the drug has a limited capacity for the drug.

Figure 1:
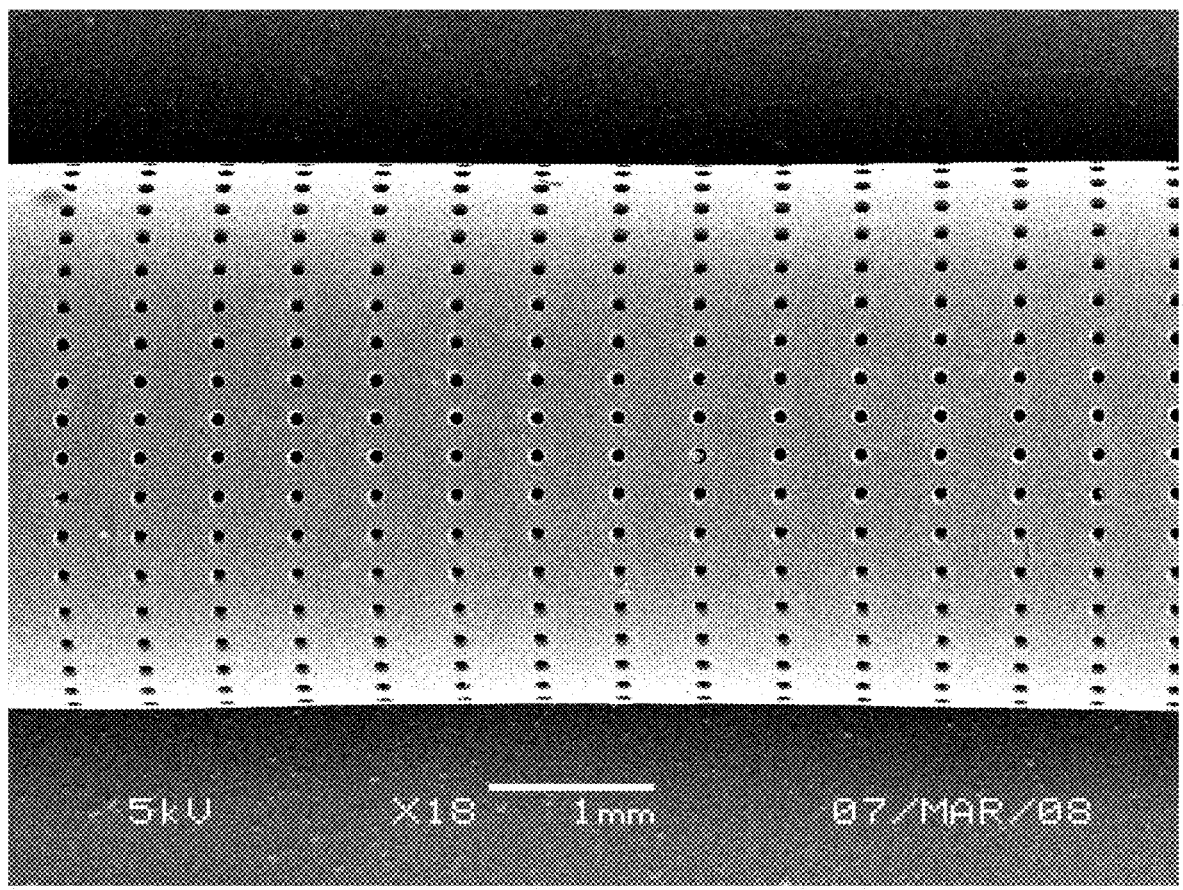
FIG. 1.
Figure 2:
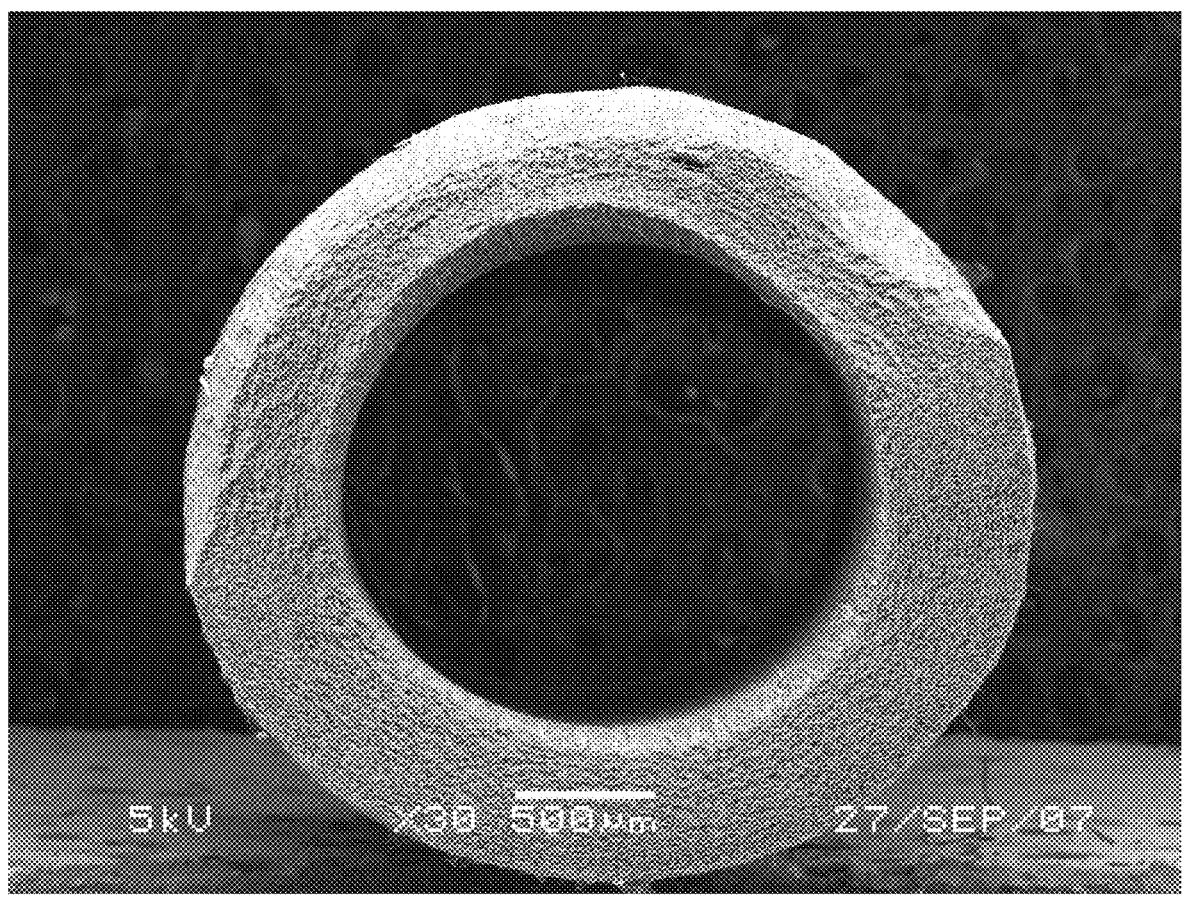
Figure 3:
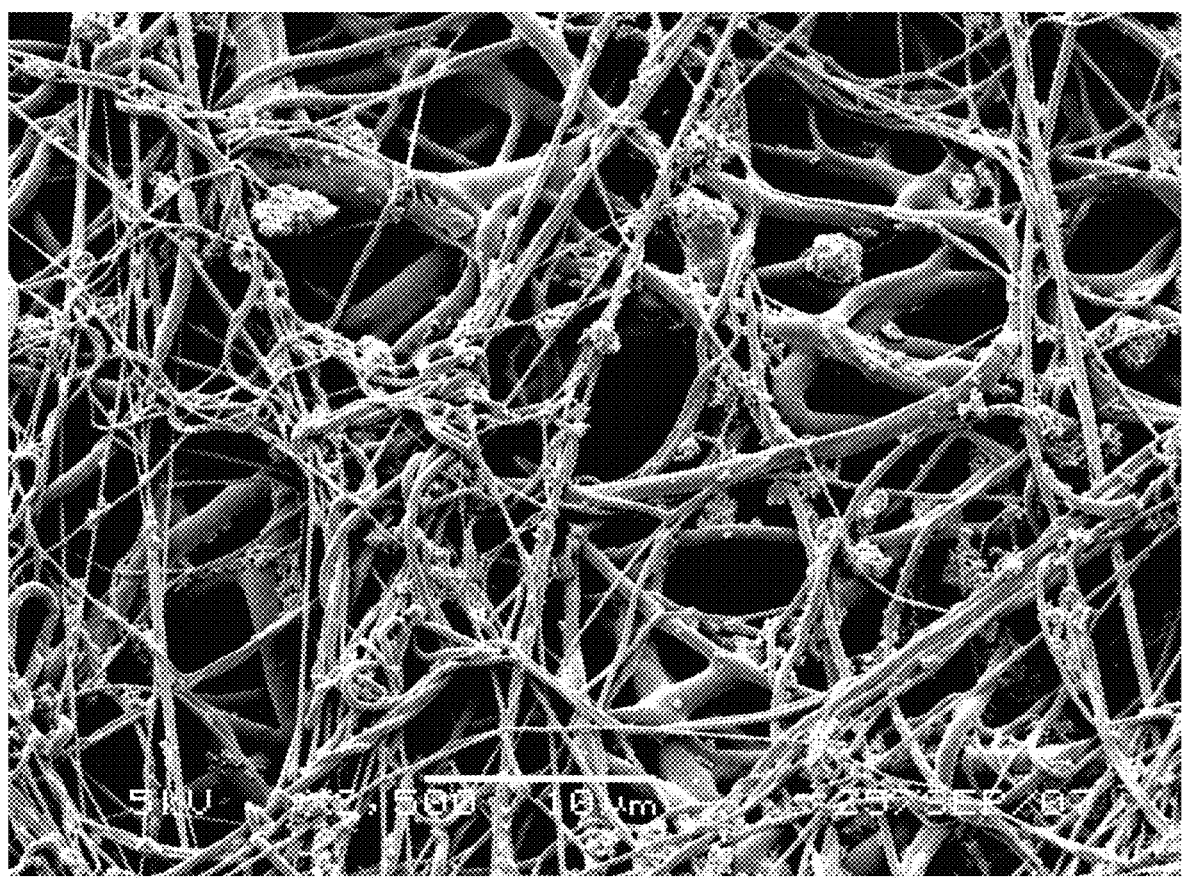
Figure 4:
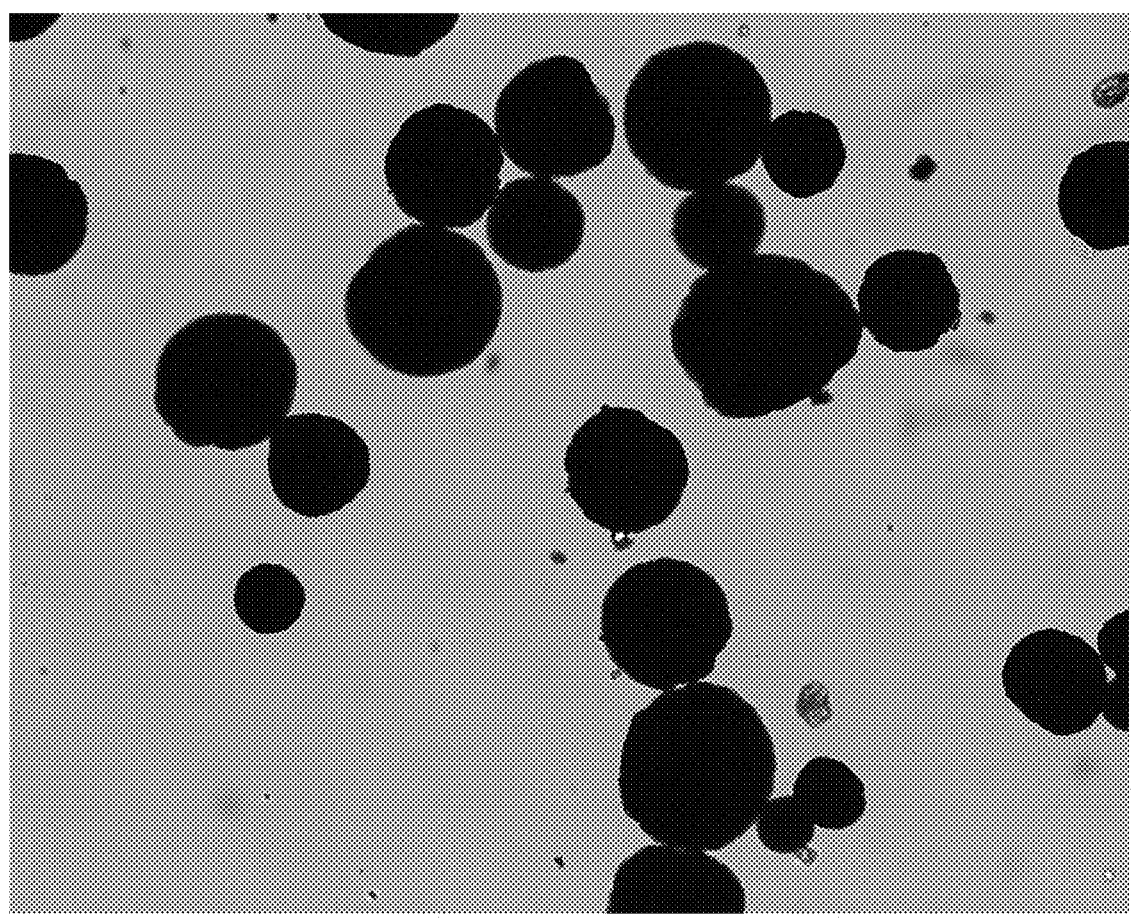
Figure 5:

Poly(dioxanone) extruded and laser machined tube. Diameter of holes is 50 microns, the number of rows of holes is 40, the number of holes per row is 60. Total number of holes is 2400. Total length of tube is 30 mm and total length of tube containing holes is 20 mm. The internal diameter of the tube is 3 mm.

FIG. 2.

Cross-section of a poly(dioxanone) tube that has been electrospun. The wall thickness is 500 microns. The inner diameter is 2 mm.

FIG. 3.

Surface of a poly(dioxanone) tube that has been electrospun. Fibers are randomly oriented and size of openings formed by fiber network is in the range of 1-20 microns.

FIG. 4.

Optical micrographs of microparticles containing 70% (w/w) TMC278 and 30% (w/w) PLGA 50/50 1A. Magnification is 100×.

FIG. 5.

Optical micrograph of microparticles containing 70% (w/w) TMC114 and 30% (w/w) PLGA 50/50 2A. Magnification is 500×.

DESCRIPTION OF THE INVENTION

The present invention relates to a degradable, removable, pharmaceutical implant for the sustained release of one or more drugs in a subject, wherein the pharmaceutical implant is composed of a tube comprising an outer wall made of a degradable polymer completely surrounding a cavity, wherein the outer wall has a plurality of openings and wherein the cavity contains one or more sets of microparticles, which micro-particles contain an active agent or a combination of two or more active agents, and wherein the size of the microparticles is selected such that the majority of the microparticles cannot pass through the openings.

The tube is composed of a degradable polymer. The microparticles contain an active ingredient or a combination of two or more active ingredients and are conceived such that they release the active ingredient upon contact with bodily fluids. The degradable polymer of which the tube is made is selected such that it does not substantially degrades before the release of the active ingredient or ingredients from the microparticles is substantially complete. The selection of the type of microparticles and their relative amounts are predicated on the specific needs of the patient subject.

As used herein, the term degradable or biodegradable means degradable by the subject, in particular animal, more in particular human, carrying the implant of the present invention. The degradation process in the subject can be, for example, an enzymatic or hydrolytical process.

In one embodiment the tube contains two or more sets of microparticles, each set containing a different active ingredient. This allows for a multi-depot system where a combination of drugs needs to be administered. In a specific embodiment the multi-depot system contains at least two, and in particular three, anti-HIV agents and the implant is used in anti-HIV therapy, which is based on the administration of a combination of anti-HIV agents.

Thus, one embodiment of the present invention relates to a degradable, removable, pharmaceutical implant for the sustained release of one drug in a subject, wherein the pharmaceutical implant is composed of a tube comprising an outer wall made of a degradable polymer completely surrounding a cavity, wherein the outer wall has a plurality of openings and wherein the cavity contains one or more sets of micro-particles, which micro-particles contain said drug, and wherein the size of the microparticles is selected such that the majority of the microparticles cannot pass through the openings. In particular, the cavity contains one set of microparticles, which micro-particles contain the drug.

One embodiment of the present invention relates to a degradable, removable, pharmaceutical implant for the sustained release of two drugs in a subject, wherein the pharmaceutical implant is composed of a tube comprising an outer wall made of a degradable polymer completely surrounding a cavity, wherein the outer wall has a plurality of openings and wherein the cavity contains two sets of microparticles, each set of microparticles containing a different drug, and wherein the size of the microparticles is selected such that the majority of the microparticles cannot pass through the openings.

One embodiment of the present invention relates to a degradable, removable, pharmaceutical implant for the sustained release of two or more drugs in a subject, wherein the pharmaceutical implant is composed of a tube comprising an outer wall made of a degradable polymer completely surrounding a cavity, wherein the outer wall has a plurality of openings and wherein the cavity contains one or more sets of micro-particles, which micro-particles contain said drugs, wherein a set of microparticles contains all drugs, contains a combination of two or more drugs but not all drugs or contains one drug, and wherein the size of the microparticles is selected such that the majority of the microparticles cannot pass through the openings. In one embodiment, when a set of microparticles contain all drugs, then preferably only one set of microparticles is present in the implant. In one embodiment, each set of microparticles contains a different drug.

The wall of the tube contains openings to allow physiological fluid to penetrate the interior cavity thereby allowing the physiological fluid to extract the drug or drugs from the microparticles and additionally to facilitate the diffusion of the drug-loaded physiological fluid from the interior of the tube to the exterior. The openings are formed to allow physiological fluid to penetrate but are too small for the microparticles to escape from the interior of the tube. Some of the microparticles may leave the implant but the size of the openings and the size of the microparticles are designed such that a majority of the microparticles is locked in the cavity of the implant. A majority of the microparticles being locked in the cavity of the implant means that at least 85% (w/w) of the microparticles are locked in the cavity of the implant;

preferably at least 90% (w/w); more preferably at least 95% (w/w); even more preferably at least 98% (w/w) or 99% (w/w) of the microparticles are locked in the cavity of the implant. In one embodiment, the size of the microparticles is selected such that the microparticles cannot pass through the openings.

Where more than one set of microparticles is present, each set of microparticles can be designed to degrade over a range of rates by varying the polymer properties used in the production of each of the microparticles in the set. This ensures drug delivery over a sustained range of time. The degradation rate of the polymer that composes the cylindrical tube is slower than the rate of degradation of the microparticles. This ensures that the implant with its contents can be removed in the case of adverse events.

Hence, the implantable removable degradable implant of the present invention functions as a depot system that can deliver one or more active ingredients over a sustained period of time. The implant of the invention is a perforated tube that contains one or more sets of microparticles, each set of microparticles containing one or more active agents. The selection of the types of actives to be delivered as well as the rate at which they are delivered can be tailored to the needs of a patient.

The tube that encases the microparticles is composed of a biocompatible, biodegradable polymer. It is necessary to select the material of composition of the tube carefully, such that the tube degrades after the microparticles degrade. This allows the removal of the drug delivery system in the case of an adverse event. Biodegradable polymers readily break down into small segments when exposed to moist body tissue. The segments then either are absorbed by the body or passed by the body. More particularly, the biodegraded segments do not elicit permanent chronic foreign body reaction, because they are absorbed by the body or passed from the body, such that no permanent trace or residual of the segment is retained by the body. Biodegradable polymers can also be referred to as bioabsorbable polymers and both terms can be used interchangeably within the context of the present invention.

Suitable biocompatible, biodegradable polymers comprise aliphatic polyesters, poly(amino acids), copoly(etheresters), polyalkylene oxalates, polyamides, poly(iminocarbonates), poly(orthoesters), polyoxaesters, polyamidoesters, polyoxaesters containing amine groups, poly(anhydrides), polyphosphazenes, and blends thereof. For the purpose of this invention aliphatic polyesters include but are not limited to homopolymers and copolymers of lactide (which includes d-, l- and meso lactic acid, and d-, l- and meso lactide), glycolide (including glycolic acid), epsilon-caprolactone, p-dioxanone (1,4-dioxan-2-one), and trimethylene carbonate. In one embodiment, the biocompatible, biodegradable polymers are copolymers of lactide (which includes d-, l- and meso lactic acid, and d-, l- and meso lactide) and glycolide (including glycolic acid). In another embodiment, the biocompatible, biodegradable polymer is a homopolymer of poly(dioxanone).

In one embodiment the tube is fabricated by electrostatic spinning. Electrostatic spinning uses an electrical force to transform polymer solutions into fibers. Spun fibers are exceedingly fine and are randomly oriented in all directions. The fibers can be spun onto a mandrel such that the fibers are continuously added on until a tube is built up. The diameter of the mandrel determines the internal diameter of the tube, from a practical standpoint of being able to contain sufficient microparticles and being easily implantable through a trocar, the diameter of the mandrel should preferably range from 1-5 mm.

The thickness of the fibers can be controlled by the concentration of polymer used in the solution that undergoes electrostatic spinning. However, a minimum polymer concentration is required for viable fibers and beyond a certain polymer concentration it is no longer possible to spin viable fibers. Although the range can vary with inherent viscosity of the polymer, a typical range is 1%-30% (w/v).

As mentioned above the design of the tube is such that it can be removed complete with its contents in the case of an adverse event. The removal is accomplished by palpating the area of implantation, finding the tube by touch, cutting a small incision into the skin adjacent to the tube and pulling the tube out through the incision. This requires that the tube has the mechanical properties to remain intact during this process. The inherent viscosity of the polymer used to fabricate the tube is the most critical factor to influence the mechanical properties. The range of the inherent viscosity to achieve adequate mechanical properties is preferably 1.5-2.5 dl/gram.

The porosity of an electrostatically spun tube (the openings of an electrostatically spun tube) is controlled to a large extent by the thickness of the walls of the tube and the diameter of the spun fiber. Thicker walls are prepared by having more fibers build up on the mandrel creating greater thickness. Due to the random orientation of the fibers in the network that is formed as more fibers are added, the total porosity of the tube decreases. Porosity is necessary since it provides a means of penetration of the surrounding physiological fluid into the tube to facilitate the diffusion of the active agent or agents from the micro-particles within. Porosity is a measure of the void spaces in a material, and is defined as the fraction or percentage of the total volume occupied by the minute open spaces. In equation form, porosity is the volume of voids divided by the total volume expressed as a fraction, between 0-1, or as a percentage, between 0-100%. There must be limits to the porosity since the microparticles must be contained within the interior of the tube. Alternatively, porosity cannot be minimized to the point that physiological fluid is prevented from penetrating into the interior of the tube. Ideally porosity should range from 60 to 90% and this can be accomplished when fabricating tubes with wall thickness that range from 50-500 microns. For instance pores ranging between 1-20 microns can be obtained with this method. Moreover, wall thickness should not be so excessive that it inhibits flexibility of the tube.

Alternatively, the tube can be fabricated from an extrusion process followed by laser drilling of holes (openings) of pre-determined size in a pre-determined pattern. As described above, the polymer that is used to fabricate the tube is biodegradable. A preferred biodegradable polymer is one that is soft and therefore flexible. Examples of polymers in this preferred group are poly(caprolactone) and poly (dioxanone). Here, the selection of inherent viscosity of the polymer is most important. The inherent viscosity should be one that provides for the polymer to be easily extruded and easily etched by a laser into a pre-determined pattern. In polymer chemistry intrinsic viscosity is related to molar mass through the Mark-Houwink equation. A practical method for the determination of intrinsic viscosity is with a Ubbelohde viscometer. Inherent viscosity and intrinsic viscosity are closely related. Intrinsic viscosity is defined as inherent viscosity in the limit of infinite dilution. In a graph of inherent viscosity versus solution concentration, the y intercept (at c=0) is equal to intrinsic viscosity. As in the case of the electrostatically spun tubing the tube must have sufficient mechanical properties that it can be pulled out from a small incision if there is an adverse event. The inherent viscosity of the polymer directly influences the mechanical properties of the tube. To meet all of these criteria the range of the inherent viscosity of the polymer should preferably range from 0.5 to 5 dl/g.

To achieve a tube-like shape the polymer is extruded from an extruder fitted with an appropriately designed die. To maintain a constant internal diameter a stream of air can be blown into the center of the tubing. Alternatively, the tubing can be extruded along a mandrel of a specific size. As in the case of the electrostatically spun tube, the internal diameter can range from 1-5 mm. The minimal wall thickness is preferably at least 25 microns; below this value the wall will not have sufficient mechanical integrity, and handling of the tube would be difficult. The maximum wall thickness should preferably not exceed 500 microns; above this value the space in the interior of the tube will be limited since the total diameter of the tube is limited by a comfortable fit in the subcutaneous space. Moreover at large wall thicknesses, the flexibility of the tube will be lowered further compromising patient comfort, and the increase in diffusion path can decrease the diffusion rate of the active(s) from the interior of the tube. The preferred range of wall thickness is 50-500 microns. The outer diameter of the tube should preferably not exceed 5 mm; above this value the implant will be too large to fit comfortably under the skin.

The pores (openings) are etched through the wall of the tubing using a low energy laser etching process. The precursor tube is mounted on a laser processing unit and subjected to energy from a laser beam in order to form an implantable device having the desired geometry or pattern imparted thereon. Low energy is important to prevent the heating of the polymer that could result in the decreased reproducibility of pore shape and diameter or even lead to a degradation of the polymer. The holes or pores have a minimum diameter of 10 microns at the outersurface of the tube, the smallest diameter pore that the laser can drill in a reproducible fashion. The upper limit of the diameter can be determined by the size of the particles. In order to prevent the loss of the majority of the micro-particles through the pores it is necessary that the diameter of the pore at the innersurface of the tube is less than an order of magnitude larger than or is the same as that of the smallest diameter micro-particles in the distribution of microparticles used in the formulation to pack the tube. (The laser etching process may result in pores with a diameter at the outersurface of the tube larger than the diameter at the innersurface of the tube.)

The pattern of the holes is imparted to the device by the use of a mask. A mask having the desired geometry or pattern is placed above the substrate and a laser beam imparts the intended pattern onto the substrate. The laser processing unit comprises a coordinated multi-motion unit that moves the laser beam in one direction and the substrate in another direction during the etching process. The laser beam is projected through the mask and ablates the bioabsorbable material, thus imparting to the device the geometry or design corresponding to the mask. An inert gas may be used in the laser-cutting environment that minimizes or eliminates, moisture and oxygen related effects during laser cutting of the material. Preferably, the laser beam is further directed through a lens before reaching the precursor material. The lens intensifies the beam and more precisely imparts the desired pattern or geometry to the substrate. A beam homogenizer may also be used to create more uniform laser beam energy and to maintain the laser beam energy consistency as the beam strikes the substrate. Beam energy can be controlled to reduce the laser cutting time.

The pores can also be formed by including a water-miscible semi-solid, surfactant, polymer or water soluble solid in the wall polymer. The pores are formed when the water-miscible or soluble substance is leached out upon contact with aqueous media.

The leaching process to form the pores can be done prior to the implantation or alternatively, can occur right after implantation when physiological media contacts the surface of the tube. Suitable water-miscible or soluble substances include phospholipids, fatty acids, Tweens, PEG's.

Drug loaded microparticles are prepared to fill the interior of the tube. By drug-loaded microparticle is meant a particle comprising a drug physically embedded in a polymer and having a particle size of less than 1,000 microns. The microparticles can be microspheres, microcapsules, or microgranules. By microsphere is meant a substantially spherical microparticle where the drug is uniformly dissolved or entrapped in the polymer. By microcapsule is meant a substantially spherical particle where the drug is coated with a polymer. By microgranule is meant an irregularly shaped microparticle wherein the active is uniformly dissolved or entrapped in the polymer.

The particle size distribution of the microparticles preferably ranges between about 1 and 1,000 microns, more preferably between about 10 and about 500 microns, and even more preferably between about 25 and about 250 microns.

The size of the microparticles or particle size distribution can be measured or determined by techniques well-known to the skilled person, such as for example by laser diffraction or microscopy. As indicated above, the microparticle size is preferably linked to the size of the openings of the tube, such that the two are coordinated to confine the microparticles within the tube.

In order to minimize the range of the particle size distribution of the microparticles, the microparticles can be sieved before being incorporated into the implants of the present invention. Sieving of the microparticles can be performed by using for example the typical mesh sieves well-known to the skilled person.

Drug loaded microparticles can be prepared using any of a large number of known processes. One preferred process, preferred because it yields microparticles with high drug loadings is the spinning disc method such as the process described in U.S. Pat. No. 7,261,529. In order to accommodate as much drug in the smallest space possible, minimizing the ultimate size of the implant, it is highly recommended to achieve loadings of at least 10% (w/w). Drug loadings of 60-80% (w/w) are preferred. To prepare the microparticles, the polymer is typically in solution in a suitable solvent. Suitable solvents include acetone, ethyl acetate, chloroform, methylene chloride. The drug is typically in solution or suspension in the suitable solvent.

Another method to prepare the drug loaded microparticles is the emulsion method. To prepare microparticles using an emulsion method, the active agent is added to an organic polymer solution either in a solid or solution state. Rapid stirring or sonication uniformly disperses the active agent throughout the polymer solution. The organic solution is subsequently poured into an aqueous solution containing surfactant to form polymer droplets within the aqueous phase and by stirring continuously the organic solvent is evaporated. The mixture is then transferred to a large vat of water and mixing continues to extract remaining solvent and harden the droplets into microparticles. The drug loaded microparticles can be collected by filtration.

The term drug is meant to include all substances that affect some biological response. The term drug encompasses drugs useful to any mammal including but not limited to human beings. The term drug includes but is not limited to the following classes of drugs: therapeutic drugs, preventative drugs, and diagnostic drugs. Examples of drugs that can be incorporated into the polymer matrix are narcotic pain relievers, gold salts, coricosteroids, hormones, anti-malarials, indole derivatives, drugs for the treatment of arthritis, anti-biotics, sulfur drugs, anti-tumor drugs, addiction-control drugs, weight control drugs, thyroid regulating drugs, analgesics, anti-hypertensive drugs, anti-inflammatory agents, anti-tussives, anti-eleptics, anti-depressants, antiarrhythmic agents, vasodilators, antihypertensive diuretics, anti-diabetic agents, anti-coagulants, anti-tubercular agents, agents for treating psychosis, agents for the treatment of Alzheimer's disease, agents for treating central nervous system disorders or syndromes, anti-HIV drugs, anti-TB agents, agents for the treatment of hepatitis, agents for the treatment of hepatitis. The above list is not meant to be comprehensive and is merely representative of the wide variety of drugs that may be incorporated into the microparticles.

Herein, the terms drug, active, active agent, active ingredient, compound, active compound are used interchangeable.

A preferred class of drugs are those used in the treatment or prevention of HIV, in particular in the treatment of HIV. These include protease inhibitors (PIs), non-nucleoside reverse transcriptase inhibitors (NNRTIs), nucleoside and nucleotide reverse transcriptase inhibitors (NRTIs and NtR-TIs). Other classes are entry inhibitors including fusion inhibitors and integrase inhibitors. For HIV treatment a so-called Highly Active Anti-Retroviral Therapy (HAART) combination is preferred. These typically comprise a backbone of two nucleoside reverse transcriptase inhibitors combined with a NNRTI or with a PI. PIs are often combined with a so-called "booster" such as ritonavir.

One embodiment concerns an implant containing a set of microparticles comprising the NNRTI rilpivirine (also referred to as "TMC278"), or a pharmaceutically acceptable salt thereof, such as the hydrochloric acid salt. Preferred is rilpivirine (=free base).

One embodiment concerns an implant wherein one set of microparticles contains a NRTI and another set of microparticles contains an NNRTI.

One embodiment concerns an implant wherein one set of microparticles contains a NNRTI and another set of microparticles contains a PI.

Another preferred class of drugs is those that are used in the treatment of hepatitis C. These include ribavirin, interferon, HCV (Hepatitis C Virus) protease inhibitors, HCV polymerase inhibitors. Also here, combinations are preferred.

One embodiment concerns an implant wherein the microparticles contain at least one drug selected from an HIV inhibitor or an HCV inhibitor.

The polymer used to fabricate the microparticles is a biocompatible, biodegradable polymer. Suitable biocompatible, biodegradable polymers comprise aliphatic polyesters, poly(amino acids), copoly(ether-esters), polyalkylene oxalates, polyamides, poly(iminocarbonates), poly(orthoesters), polyoxaesters, polyamidoesters, polyoxa-esters containing amine groups, poly(anhydrides), polyphosphazenes, and blends thereof. For the purpose of this invention aliphatic polyesters include but are not limited to homopolymers and copolymers of lactide (which includes d-, l- and meso lactic acid, and d-, l- and meso lactide), glycolide (including glycolic acid), epsilon-caprolactone, p-dioxanone (1,4-dioxan-2-one), and trimethylene carbonate (1,3-dioxan-2-one). In one embodiment, the biocompatible, biodegradable polymers are copolymers of lactide (which includes d-, l- and meso lactic acid, and d-, l- and meso lactide) and glycolide (including glycolic acid). In another embodiment, the biocompatible, biodegradable polymer is a co-polymer of lactide and glycolide with a mole percent of lactide that ranges from 85% to 50%.

In one embodiment of the present invention the microparticles contain in addition to the polymer and the one or more drugs, a surfactant. Surfactants are utilized to improve the wetability of hydrophobic components and they are typically ampiphilic molecules that contain both hydrophilic and lipophilic groups. The hydrophile-lipophile balance (HLB) number is used as a measure of the ratio of these groups. It is a value between 0-60 defining the affinity of a surfactant for water or oil. HLB numbers are calculated for nonionic surfactants using the molecular weights of the hydrophilic and hydrophobic portions of the molecule, and these surfactants have numbers ranging from 0-20. The HLB values that are associated with ionic surfactants are not calculated but rather they are given a value based on its relative or comparison surfactant behavior.

Surfactants with HLB numbers >10 have an affinity for water (hydrophilic) and surfactants with HLB number <10 have an affinity for oil (lipophilic).

Surfactants include non-ionic surfactants and ionic surfactants. The ionic surfactants include cationic, anionic and zwitterionic surfactants such as the fatty acid salts e.g. sodium oleate, sodium lauryl sulfate, sodium lauryl sarcosinate, sodium dioctyl sulfosuccinate, sodium myristate, sodium palmitate, sodium state, sodium ricinoleate and the like; such as bile salts e.g. sodium cholate, sodium taurocholate, sodium glycocholate and the like; such as phospholipids e.g. egg/soy lecithin, hydroxylated lecithin, lysophosphatidylcholine, phosphatidylcholine, phosphatidyl ethanolamine, phosphatidyl glycerol, phosphatidyl serine and the like; such as phosphoric acid esters e.g. diethanolammonium polyoxyethylene-10 oleyl ether phosphate, esterification products of fatty alcohols or fatty alcohol ethoxylates with phosphoric acid or anhydride; such as carboxylates e.g. succinylated monoglycerides, sodium stearyl fumarate, stearoyl propylene glycol hydrogen succinate, mono/diacetylated tartaric acid esters of mono- and diglycerides, citric acid esters of mono- and diglycerides, glyceryl-lacto esters of fatty acids, lactylic esters of fatty acids, calcium/sodium stearoyl-2-lactylate, calcium/sodium stearoyl lactylate, alginate salts, propylene glycol alginate, ether carboxylates and the like; such as sulfates and sulfonates e.g. ethoxylated alkyl sulfates, alkyl benzene sulfates, alpha-olefin sulfonates, acyl isethionates, acyl taurates, alkyl glyceryl ether sulfonates, octyl sulfosuccinate disodium, disodium undecyleneamido-MEA-sulfosuccinate and the like; such as cationic surfactants e.g. hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (lauryl betaine), ethoxylated amines (polyoxyethylene-15 coconut amine) and the like.

Preferred surfactants in the present invention are non-ionic surfactants.

Suitable non-ionic surfactants which may be used in the present invention comprise:

a) Polyethylene glycol fatty acid monoesters comprising esters of lauric acid, oleic acid, stearic acid, ricinoic acid and the like with PEG 6, 7, 8, 9, 10, 12, 15, 20, 25, 30, 32, 40, 45, 50, 55, 100, 200, 300, 400, 600 and the like, for instance PEG-6 laurate or stearate, PEG-7 oleate or laurate, PEG-8 laurate or oleate or stearate, PEG-9 oleate or stearate, PEG-10 laurate or oleate or stearate, PEG-12 laurate or oleate or stearate or ricinoleate, PEG-15 stearate or oleate, PEG-20 laurate or oleate or stearate, PEG-25 stearate, PEG-32 laurate or oleate or stearate, PEG-30 stearate, PEG-40 laurate or oleate or stearate, PEG-45 stearate, PEG-50 stearate, PEG-55 stearate, PEG-100 oleate or stearate, PEG-200 oleate, PEG-400 oleate, PEG-600 oleate; (the surfactants belonging to this group are for instance known as Cithrol, Algon, Kessco, Lauridac, Mapeg, Cremophor, Emulgante, Nikkol, Myrj, Crodet, Albunol, Lactomul)

b) Polyethylene glycol fatty acid diesters comprising diesters of lauric acid, stearic acid, palmic acid, oleic acid and the like with PEG-8, 10, 12, 20, 32, 400 and the like, for instance PEG-8 dilaurate or distearate, PEG-10 dipalmitate, PEG-12 dilaurate or distearate or dioleate, PEG-20 dilaurate or distearate or dioleatePEG-32 dilaurate or distearate or dioleate, PEG-400 dioleate or distearate; (the surfactants belonging to this group are for instance known as Mapeg, Polyalso, Kessco, Cithrol)

c) Polyethylene glycol fatty acid mono- and diester mixtures such as for example PEG 4-150 mono and dilaurate, PEG 4-150 mono and dioleate, PEG 4-150 mono and distearate and the like; (the surfactants belonging to this group are for instance known as Kessco)

d) Polyethylene glycol glycerol fatty acid esters such as for instance PEG-20 glyceryl laurate or glyceryl stearate or glyceryl oleate, PEG-30 glyceryl laurate or glyceryl oleate, PEG-15 glyceryl laurate, PEG-40 glyceryl laurate and the like; (the surfactants belonging to this group are for instance known as Tagat, Glycerox L, Capmul), e) Alcohol-oil transesterification products comprising esters of alcohols or polyalcohols such as glycerol, propylene glycol, ethylene glycol, polyethylene glycol, sorbitol, pentaerythritol and the like with natural and/or hydrogenated oils or oil-soluble vitamins such as castor oil, hydrogenated castor oil, vitamin A, vitamin D, vitamin E, vitamin K, an edible vegetable oil e.g. corn oil, olive oil, peanut oil, palm kernel oil, apricot kernel oil, almond oil and the like, such as PEG-20 castor oil or hydrogenated castor oil or corn glycerides or almond glycerides, PEG-23 castor oil, PEG-25 hydrogenated castor oil or trioleate, PEG-35 castor oil, PEG-30 castor oil or hydrogenated castor oil, PEG-38 castor oil, PEG-40 castor oil or hydrogenated castor oil or palm kernel oil, PEG-45 hydrogenated castor oil, PEG-50 castor oil or hydrogenated castor oil, PEG-56 castor oil, PEG-60 castor oil or hydrogenated castor oil or corn glycerides or almond glycerides, PEG-80 hydrogenated castor oil, PEG-100 castor oil or hydrogenated castor oil, PEG-200 castor oil, PEG-8 caprylic/capric glycerides, PEG-6 caprylic/capric glycerides, lauroyl macrogol-32 glyceride, stearoyl macrogol glyceride, tocopheryl PEG-1000 succinate (TPGS); (the surfactants belonging to this group are for instance known as Emalex, Cremophor, Emulgante, Eumulgin, Nikkol, Thornley, Simulsol, Cerex, Crovol, Labrasol, Softigen, Gelucire, Vitamin E TPGS), f) polyglycerized fatty acids comprising polyglycerol esters of fatty acids such as for instance polyglyceryl-10 laurate or oleate or stearate, polyglyceryl-10 mono and dioleate, polyglyceryl polyricinoleate and the like; (the surfactants belonging to this group are for instance known as Nikkol Decaglyn, Caprol or Polymuls)

g) Sterol derivatives comprising polyethylene glycol derivatives of sterol such as PEG-24 cholesterol ether, PEG-30 cholestanol, PEG-25 phyto sterol, PEG-30 soya sterol and the like; (the surfactants belonging to this group are for instance known as Solulan™ or Nikkol BPSH)

h) Polyethylene glycol sorbitan fatty acid esters such as for example PEG-10 sorbitan laurate, PEG-20 sorbitan monolaurate or sorbitan tristearate or sorbitan monooleate or sorbitan trioleate or sorbitan monoisostearate or sorbitan monopalmiate or sorbitan monostearate, PEG-4 sorbitan monolaurate, PEG-5 sorbitan monooleate, PEG-6 sorbitan monooleate or sorbitan monolaurate or sorbitan monostearate, PEG-8 sorbitan monostearate, PEG-30 sorbitan tetraoleate, PEG-40 sorbitan oleate or sorbitan tetraoleate, PEG-60 sorbitan tetrastearate, PEG-80 sorbitan monolaurate, PEG sorbitol hexaoleate (Atlas G-1086) and the like; (the surfactants belonging to this group are for instance known as Liposorb, Tween, Dacol MSS, Nikkol, Emalex, Atlas)

i) Polyethylene glycol alkyl ethers such as for instance PEG-10 oleyl ether or cetyl ether or stearyl ether, PEG-20 oleyl ether or cetyl ether or stearyl ether, PEG-9 lauryl ether, PEG-23 lauryl ether (laureth-23), PEG-100 stearyl ether and the like; (the surfactants belonging to this group are for instance known as Volpo, Brij)

j) Sugar esters such as for instance sucrose distearate/monostearate, sucrose monostearate or monopalmitate or monolaurate and the like; (the surfactants belonging to this group are for instance known as Sucro ester, Crodesta, Saccharose monolaurate)

k) Polyethylene glycol alkyl phenols such as for instance PEG-10-100 nonyl phenol (Triton X series), PEG-15-100 ocyl phenol ether (Triton N series) and the like;

l) Polyoxyethylene-polyoxypropylene block copolymers (poloxamers) such as for instance poloxamer 108, poloxamer 188, poloxamer 237, poloxamer 288 and the like; (the surfactants belonging to this group are for instance known as Synperonic PE, Pluronic, Emkalyx, Lutrol™, Supronic, Monolan, Pluracare, Plurodac)

More preferred surfactants are non-ionic surfactants with HLB values of 20 or less. A suitable surfactant is F108 (BASF).

To facilitate the loading of the microparticles into the tubes a hydrogel can be used as a binder to bind together the different sets of microparticles prior to the loading of the micro-particles into the tubes. Binders can be carefully selected to not only bind but to serve as a means to wick moisture into the interior of the tube facilitating drug diffusion particularly when microparticles are composed of hydrophobic drugs. Moreover, the binder can be chosen to actually enhance the solubility of poorly water soluble compounds formulated into the microparticles. This can be accomplished by for instance providing a low pH environment for those compounds that are more soluble at low pH. Alternatively, the binder can be a polymer that self-emulsifies in a hydrated system providing a surfactant environment for poorly water-soluble drugs incorporated into the microparticles. Some examples of binders include albumin, casein, waxes, starch, crosslinked starch, simple sugars, glucose, polysucrose, polyvinyl alcohol, gelatine, modified celluloses, carboxymethylcellulose, hydroxymethylcellulose, hydroxyethylcellulose, hydroxypropylcellulose, hydroxypropyl-ethylcellulose, hydroxypropyl-methyl cellulose, sodium carboxymethyl cellulose, cellulose acetate, sodium alginate, hyaluronic acid, hyaluronic acid derivatives, polyvinyl pyrrolidone, polymaleic anhydride esters, polyortho esters, polyethyleneamine, glycols, polyethylene glycol, methoxypolyethylene glycol, ethoxypolyethylene glycol, polyethylene oxide, poly(1,3 bis(p-carboxyphenoxy) propane-co-sebacic anhydride, N,N-diethylaminoacetate, block copolymers of polyoxyethylene and polyoxypropylene, polyacrylic acid and polyacrylic acid derivatives, guar gum, carob ban gum, chitins, self emulsifying polymers or agents. An effective amount of binder is one with sufficient viscosity to bind the particles but with a low solids content in order to minimize the amount of space it requires in the interior of the tube.

In one embodiment of the present invention the hydrogel itself contains one or more drugs in addition to the one or more drugs present in the microparticles. This facilitates in obtaining high initial plasma concentrations of the one or more drugs.

The microparticles or microparticle/hydrogel mixture can be introduced in the tubes by manual techniques or by automatic techniques. Manual techniques include the transfer of mixture by spatula into the tube. Automatic techniques include the use of conventional filling machines used in the pharmaceutical industry.

To close the tube to completely surround the cavity, the ends of the tubes can be heat sealed. This can be accomplished for instance by using a Bovie low temperature surgical cautery. Prior to applying heat, a small piece of tubing material is first inserted into the end section of the tubing being sealed and then heat is applied to the local end area to make the material melt; the end can then be squeezed by hand to form a seal. One end of the tube is first sealed and then the tubing is filled with the designated content. After that, the open end can be sealed in the same way. There are many other possible ways to seal the ends. For example, a regular heat sealer can be used where the end section of the tubing to be sealed is placed in between the two lips of the sealer. Sealing is accomplished by applying heat and pressure at the same time.

The ends may also be glue sealed by using a suitable adhesive; small amount of the adhesive can be placed inside the tubing in the tip area and then pressure is applied to compress the tip of the end. Typically a pre-determined holding time is necessary to form a solid seal.

The implant may have any shape including but not limited to a disc, sphere or cylinder but preferably the implant is a cylinder. The size of the cylinder can be between 1 and 5 mm in diameter and 0.5 and 5 cm in length, more preferably between 1 and 4 mm in diameter and 1 and 5 cm in length. It is particularly useful in anti-virus therapy such as anti-HIV therapy and anti-hepatitis therapy.

EXAMPLES

Example 1

A binder solution was prepared using poly(acrylic acid) (PAA) (Aldrich) of molecular weight 1.25 million kilodaltons. Three hydrogel solution concentrations were prepared using deionized water to dissolve the poly(acrylic acid). The concentrations were 5% (w/w), 0.5% (w/w), 0.25% (w/w). Although mixtures of microparticles were obtained with all 3 hydrogels, the mixture easiest to work with in terms of not being too viscous to make dispersion of microparticle in the hydrogel difficult and in terms of the hydrogel not being too runny for easy loading into the tube was the 0.5% (w/w). The pH of each hydrogel was measured using pH paper, the pH of the 5% hydrogel was between 2-3, the other two hydrogels measured 3.

The particle/hydrogel mixture can be prepared such that it is one part hydrogel and 2 parts microparticles and in this way minimizing the space in the tube that is required by the gel and maximizing the internal space for the microparticles. Microparticles composed of 70% (w/w) TMC278 and 30% (w/w) poly(lactic co-glycolic acid) (PLGA) (DLG 5050 1A Surmodics Pharmaceuticals, Birmingham, Ala.) were prepared using the spinning disc method. In general, to prepare particles using the spinning disc method, a disc of specific size is selected and mounted on a motor with a tunable rotation rate to control disc speed. The polymer is dissolved in a suitable solvent, such as for example acetone, and the drug is added to the polymer solution and stirred. The resulting mixture is fed to the disc at a specific rate. As the disc spins, centripetal force forms droplets or particles to the outer edge of the disc. The particles are directed to a drying cone that is pre-set with a gradient of temperatures. The solvent is removed from the particles in this drying step causing the particles to harden or solidify and the particles are collected.

In this example, a 4% (w/v) PLGA solution was prepared in acetone. The disc (Southwest Research Institute, San Antonio, Tex.) speed was 9250 rpm, the disc size was 7.62 cm, the feed rate was 45 g/min, cone outlet temperature ranged from 45-48° C. The TMC278 was added into the PLGA solution and stirred for approximately 15-20 minutes before being fed into the disc. The particle size distribution was measured using a Malvern Mastersizer (Malvern Instruments, Ltd, Worcestershire, UK. Results: the $d_{10}$ was 29 microns, the $d_{50}$ was 48 microns and the $d_{90}$ was 69 microns.

The tubes were prepared by electrostatic spinning of a 120 mg/ml poly(dioxanone) in hexafluoroisopropanol. The inner diameter of the tube was 3 mm and the wall thickness was 500 microns. The length of the tube used was 2.54 cm. Scanning electron microscopy (JEOL JSM 5900LV, Tokyo, Japan) analysis of the tubes indicated that the openings (pores) in the network formed by the randomly oriented fibers were in the range of 1-20 microns. Initially, one end of the tubes was heat sealed. Heat sealing was accomplished using a Bovie low temperature surgical cautery. Prior to applying heat, a small piece of the tubing material was first inserted into the end section of the tubing being sealed and then heat was applied to the local end area to make the material melt; the end was then squeezed by hand to form a seal. After the one end was sealed, the tube was weighted together with a small piece of tubing material that will be added to the other end of the tube when this end will be heat sealed (mass of the empty tube was noted) and subsequently filled with the microparticle/hydrogel mixture using a spatula. The filling was followed by heat sealing of the second end of the tube using the same procedure as outlined above (with the addition of the small piece). The sealed tube was weighed. The difference in weight between the filled and unfilled tube is equal to mass of the contents. Details of the contents of each tube are summarized in Table 1.

TABLE 1

Electrostatically spun tubes with microparticle/PAA mixture

| Sample ID | Concentration of gel (w/w) | pH of gel | Mass of contents in tube (mg) (microparticle/ hydrogel mixture) | Mass of TMC278 in tube (mg) |
|---|---|---|---|---|
| 3895-42-1 | 5% | 2-3 | 45.12 | 16 |
| 3895-42-2 | 0.5 | 3 | 59.83 | 21 |
| 3895-42-3 | 0.25 | 3 | 36.1 | 17 |

The samples were placed in a Method I sampling system using a Hanson Dissolution Tester (Hanson Research Corp., Chatsworth, Calif.) using 500 ml elution vessels. The media was 500 ml distilled water and samples were taken at 1, 3, 7, 10, and 14 days. The release data are summarized in Table 2. Experiments were performed at 37° C.

TABLE 2

TMC278 elution from poly(acrylic acid) gels in electrospun tubes

| Time (Day) | 3895-42-1 micrograms eluted/ % of total load | 3895-42-2 micrograms eluted/ % of total load | 3895-42-3 micrograms eluted/ % of total load |
|---|---|---|---|
| 1 | 434/2.7 | 444/2.1 | 429/2.5 |
| 3 | 445/2.8 | 398/1.9 | 408/2.4 |
| 7 | 443/2.8 | 388/1.8 | 400/2.3 |
| 10 | 443/2.8 | 402/1.9 | 381/2.2 |
| 14 | 448/2.8 | 399/1.9 | 406/2.4 |

The solubility of TMC278 dramatically increases at pH=2. Solubility experiments demonstrate that the solubility in water is 950 times greater at pH of 2 relative to pH of 7. The use of an acidic binder gel that can effectively lower pH, can increase the rate of elution of TMC278 from the polymer matrix. Increasing the concentration of the acidic polymer in the gel can depress the pH even further (Table 1). As illustrated in Table 2, dispersing the TMC278 microparticles in a 5% (w/w) poly(acrylic acid) gel where the pH is between 2 and 3, results in a larger amount of TMC278 eluting from the microparticles relative to TMC278 microparticles dispersed in the less concentrated hydrogels, where the pH is 3.

Example 2

A 3% (w/v) of carboxymethylcellulose (CMC; Hercules, 7H3SFPH) gel was prepared in PBS. When prepared in water the viscosity of the gel would be 3000-6000 cps. However the viscosity of the polymer drops by ⅔ when prepared in a salt solution due to its sensitivity to ionic strength and therefore does readily mix with the microparticles. Microparticles composed of 70% (w/w) TMC278 and 30% (w/w) poly(lactic co-glycolic acid) (PLGA) (DLG 5050 1A, Surmodics Pharmaceuticals, Birmingham, Ala.) were prepared using the spinning disc method. In short, a 4% (w/v) polymer solution was prepared in acetone. The disc speed and size were 9250 rpm and 7.62 cm, respectively. The feed rate was 45 g/min and the cone outlet temperature ranged from 45-48° C. The TMC278 was added into the PLGA solution and stirred for approximately 15-20 minutes before being fed into the disc. The particle size distribution was measured using a Malvern Mastersizer (Malvern Instruments, Worcestshire, UK). Results indicated the $d_{10}$ at 29 microns, the $d_{50}$ at 48 microns and the $d_{90}$ at 69 microns. A 2 mg sample of the microparticles was mixed with 2 ml of the 3% CMC gel. The total loading of TMC278 in this mixture was 2.25% (w/w).

Poly(lactic co-glycolic acid) with a molar ratio of 85/15 of lactide/glycolide was used to prepare the tubing. The tubing was extruded using a small scale, commercial extrusion line comprised of a 1" single screw extruder (Davis Standard), a water cooling trough, a puller and a cutter. An in-line laser diameter measuring system was also used to monitor the diameter and the roundness of the tubing. In the extrusion process, the raw material in resin form was fed from a top mounted hopper into the barrel of the extruder where the rotating screw forced the resin forward into the barrel which was heated to the desired melt temperature. In the three heating zones of the extruder a suitable temperature profile was set and maintained. This allowed the plastic resin to melt gradually as it was pushed through the barrel (lower risk of overheating which may cause degradation of the polymer).

At the front end of the barrel, the molten plastic left the screw and traveled through a screen pack to remove any contaminants in the melt which also helped to establish a more stable back pressure. After passing through the breaker plate molten plastic entered the die. The die was tubular with a mandrel in the center to create an annular structure for the creation of tubular profile. Small amount of air was injected inside of the polymer tubing through the tip of the mandrel (air flow rate controlled by an air flow controller). The extrudate in the form of tubing was pulled by a downstream rubber roller through a cooling water trough where the tubing was cooled and solidified. Downstream to the puller was a cuter where the extruded tubing with the final size was cut to pre-determined length and collected. An in-line laser diameter measuring system was installed after the cooling trough and before the puller for continuous in-line measuring and monitoring of the extruded tubing dimensions.

The extruded tube was perforated with 10 micron holes using a laser. A pattern of 20 rows X 20 columns of holes was used to perforate the polymer tubing. The interior diameter of the tube was 1.5 mm and the outer diameter was 1.6 mm. A 2.54 cm sample was cut from the tubing and heat sealed on one end (according to the same procedure as described in example 1). A 33.67 mg sample of the microparticle/CMC gel mixture was transferred into the perforated tube by using a spatula and the second end of the tube was heat sealed as described above.

The sample was placed in a Method I sampling system in a Hanson Dissolution Tester (Chatsworth, Calif.) using 500 ml vessels. The media was 500 ml distilled water. Samples were taken at 1, 3, 7, 10, and 14 days. The release data is summarized in Table 3. Experiments were performed at 37° C.

TABLE 3

| TMC278 release from microparticle in a perforated tube | | |
|---|---|---|
| Day | Cumulative amount of TMC278 (micrograms) released | Cumulative Release of TMC278; (Percent of Total load) |
| 1 | 58 | 7.6 |
| 3 | 59 | 7.8 |
| 7 | 112 | 14.7 |
| 10 | 125 | 16.4 |
| 14 | 138 | 18.2 |

Example 3

A 0.5% (w/w) poly(acrylic acid) (Aldrich) gel was prepared in water and 400 mg of the gel was mixed with 960 mg of TMC278 particles. Microparticles were composed of 70% (w/w) of TMC278 and 30% (w/w) poly(lactic co-glycolic acid) (DLG 5050 1A, Surmodics Pharmaceuticals, Birmingham, Ala.) and prepared according to the procedure described in Example 1 and 2). The particle size distribution of the microparticles was measured as described above; $d_{10}$ was 29, $d_{50}$=48 and $d_{90}$ was 68 microns. The mixture was packed into a poly(dioxanone) tube which was prepared according to the procedure described in Example 2. The tube was perforated using laser technology as described above. The tube was 30 mm long, 5 mm sections from each edge were unperforated. The perforations in the 30 mm length in the middle section were arranged in 40 rows of holes and 2400 holes per row. The diameter of each hole was 50 microns. The mass of the tube before filling was 102.01 mg. The mass of the tube after filling was 190.64 mg (the calculated concentration of TMC278 in the tube is 43.4 mg).

Two more samples were prepared in this fashion, and the mass of the microparticle/gel mixture in the tube was 53.7 mg and 46.3 mg, respectively. HPLC analysis confirmed the content of 39.2 and 32.1 mg of TMC278 in the respective tubes.

Example 4

Electrostatically spun poly(dioxanone) tubes were prepared using a 120 mg/ml polymer solution in hexafluoroisopropanol. The wall thickness of the tube was 500 microns. A microparticle mixture was prepared using microparticles with a particle size distribution of $d_{10}$=29, $d_{50}$=48 and $d_{90}$=68 microns. The composition of the microparticles was 70% (w/w) TMC278 and 30% (w/w) PLGA 50/50 (0.1 dl/g). A sample of 1200 mg of microparticles was mixed with 500 mg of a 0.5% poly(acrylic acid) aqueous gel. The mass of the 2 cm long tube before filling was 82.8 mg and 203.0 mg after filling.

Example 5

The microparticle mixture described in Example 4 was used to fill an electrostatically spun tube that was prepared from a 150 mg/ml polydioxanone solution, as prepared in Example 1. The wall thickness of the tube was 200 microns. The mass of the 2 cm tube before filling was 29.0 mg and after filling was 129.3 mg.

Example 6

The microparticle mixture described in Example 4 was used to fill an electrostatically spun tube that was prepared from a 60 mg/ml polydioxanone solution, as prepared in Example 1. The wall thickness of the tube was 500 microns. The mass of the 2 cm tube before filling was 55.4 mg and after filling was 151.9 mg.

Example 7

Two different sets of microparticles containing TMC278 were prepared. One set of microparticles was prepared using 4% (w/v) poly(lactic co-glycolic acid) (DLG 5050 2A, Surmodics Pharmaceuticals, Birmingham, Ala.) acetone solution. The micro-particles were prepared using spinning disc method as described in Example 1. The disc speed was 7500 rpm and the disc size was 7.62 cm. The feed rate was 45 g/min and the cone outlet temperature was 45-48° C. The majority of the particles formed were in the range of 50-75 microns, and the loading of TMC278 in the particles was 70% (w/w). The second set of microparticles were prepared from 4% (w/v) poly(lactic co-glycolic acid) (DLG 5050 1A, containing 2.5% (w/w) oligomers of lactide-glycolide (5050 DLG 1CA, Surmodics Pharmaceutics, Birmingham, Ala.) in acetone solution. TMC278 loading in the second set of microparticles was also 70% w/w. These were also prepared using a spinning disc method. The disc speed was 9250 rpm, the feed rate was 50-55 g/min, and the cone outlet temp was 45° C. A sample of 519 mg of 0.5% poly(acrylic acid) aqueous gel was mixed with 606 mg of the TMC278 microparticles prepared from the DLG 5050 2A polymer and 599 mg of TMC278 particles prepared with the DLG 5050 1A with added DLG 1CA. A poly(dioxanone) perforated tube as described in Example 3 was filled with the microparticle mixture. The mass of the empty tube was 85.01 mg and the mass of the tube filled with the microparticle mixture was 211 mg.

Example 8

Two different sets of microparticles were prepared, one set contained TMC278, a potent non-nucleoside reverse transcriptase inhibitor for the treatment of HIV. The second set contained TMC114, a protease inhibitor for the treatment of HIV, also known as darunavir. The TMC278 microparticles were prepared using the spinning disc method as described above. For these particles, a 4% (w/v) poly(lactide co-glycolide) (5050 DLG 1A, Surmodics Pharmaceuticals, Birmingham, Ala.) acetone solution with added 7.5% (w/v) oligomeric poly(lactide co-glycolide) (5050 DLG 1CA, Surmodics Pharmaceutical, Birmingham, Ala.) was prepared. The loading of TMC278 relative to the polymer was 70% (w/w). Particles sizes ranged from 20-75 microns.

The second set of microparticles was prepared by dissolving TMC114 into a 4% (w/v) poly(lactide co-glycolide) (5050 DLG 1A, Surmodics Pharmaceuticals, Birmingham, Ala.) acetone solution. The drug-polymer solution was fed onto a 7.62 cm disc that was spinning at 9500 rpm at a feed rate of 45 g/min. The disc chamber outlet temperature (cone outlet temperature) was 42-45° C., and the loading of TMC114 in the microparticles was 70% (w/w). A mixture of the microparticles was prepared by preparing a 0.5% (w/w) poly(acrylic acid) aqueous gel and mixing 507 mg of the gel with 502 mg of the TMC78 microparticles and 507 mg of the TMC114 microparticles. Microparticle mixture was packed into a poly(dioxanone) extruded and perforated tube (see Example 3). Pattern of perforations and size of perforations are described in Example 3. As noted earlier, the tube was initially heat-sealed on one end, filled with mixture, and heat-sealed on the other end. Five different samples were prepared and elution rate of the two drugs was measured (Table 4). The media used to measure elution rate was 90% (v/v) methanol and 10% (v/v) water due to the extreme insolubility of TMC278 in water.

TABLE 4

Cumulative release of TMC114 and TMC278 from microparticles sequestered in poly(dioxanone) extruded and perforated tubes

| Sample # | Mass of microparticle/gel mixture (mg) | TMC114 1 day (mg) | TMC114 3 days (mg) | TMC114 7 day (mg) | TMC278 1 day (mg) | TMC278 3 day (mg) | TMC278 7 day (mg) |
|---|---|---|---|---|---|---|---|
| 3998-8-1 | 62.93 | 3.0 | 16 | 22 | 7.1 | 13.1 | 21.4 |
| 3998-8-2 | 80.71 | 3.5 | 20 | 33 | 8.5 | 15.7 | 35.5 |
| 3998-8-3 | 72.88 | 4.0 | 19 | 19 | 8.4 | 16.5 | 19.5 |
| 3998-8-4 | 74.96 | 4.0 | 22 | 28 | 9.8 | 16.8 | 25.4 |
| 3998-8-58-5 | 66.77 | 3.8 | 22 | 22 | 9.3 | 14.8 | 19.7 |

Example 9

In vivo testing of electrostatically spun tube containing two sets of microparticles Tubes were electrostatically spun from a 100 mg/ml polydioxanone ($IV_{HFIP}$=1.99 dl/g) hexafluoroisopropanol solution. A 4 mm mandrel was used to provide a consistent inner diameter of 4 mm. The rotational speed of the mandrel was 400 rpm, the charging voltage range was 20/−10 kV, and the pump flow rate was 10 ml/hour. The resulting wall thickness was 500 microns. Fiber diameters were 1-2 microns and the average pore size formed from the network of fibers was 20 microns as determined by Scanning Electron Microscopy.

The microparticles were prepared by the spinning disc method using a polymer/acetone solution with a concentration ranging from 3-4% (w/w). Two sets of microparticles were prepared. The target composition of one set was 70% (w/w) TMC278 and 30% (w/w) PLGA 50/50 (Lakeshore Biomaterials $IV_{HFIP}$=0.79 dl/g). The target composition of the other set of microparticles was 70% (w/w) of compound 1 (=compound 14 of WO01/25240) and 30% (w/w) PLGA 50/50 (Lakeshore Biomaterials $IV_{HFIP}$=0.18 dl/g). This compound 1 has the following structure and will be referred to hereinafter as compound 1:

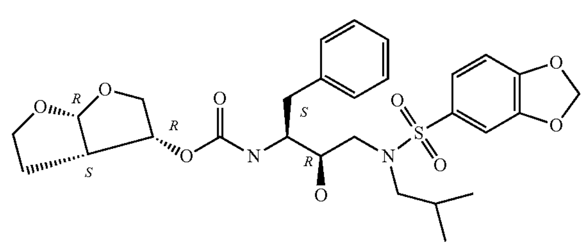

The disc speed ranged from 7300-7500 rpm, cone inlet and outlet temperatures were 56-57° C. and 33.5° C., respectively. The loading of TMC278 and compound 1 in the respective microparticles was measured by HPLC, and TMC278 and compound 1 concentrations were 65% (w/w) and 35% (w/w) respectively. The difference between the target and actual concentration for compound 1 illustrates the greater difficulty in encapsulation of compound 1.

The microparticle size range was determined by placing a randomly selected sample on the stage of an optical microscope and using a ruler to measure the various sizes of the microparticles in the randomly selected sample. The resulting size range of the TMC278 microparticles was 10-100 micron, and that of the compound 1 microparticles was 20-100 microns.

Mixing of the two types of microparticles was accomplished by transferring both sets of microparticles into a 50 mL glass roundbottom flask and mixing with an overhead mixer fitted with a glass stirring rod and teflon paddle. The microparticles were dry-mixed at 100 rpm for 30 minutes (previously determined to be a sufficient mixing time to achieve a homogeneous reproducible mixture of both microparticles).

Approximately 133 mg of the microparticle mixture was introduced into the electrostatically prepared tubes using a spatula.

The prepared tubes were implanted into the subcutaneous space on the back of four male Sprague-Dawley rats weighing between 250-350 grams. The dose of TMC278 was 139 mg/kg and the dose of compound 1 was 64 mg/kg. The tail vein was sampled at pre-determined time points. Blood samples were immediately centrifuged to extract the plasma, plasma was analyzed for compound 1 and TMC278 by LC/MS/MS. The lower limit of quantitation was 0.4 ng/ml and 2 ng/ml for TMC278 and compound 1, respectively. Values for the tested plasma concentrations at each time point for each drug are tabulated in Table 5.

TABLE 5

TMC278 and compound 1 plasma concentrations

| Drug | Animal # | 3 hour ng/ml | 1 day ng/ml | 3 day ng/ml | 7 day ng/ml | 14 day ng/ml | 28 day ng/ml | 35 day ng/ml |
|---|---|---|---|---|---|---|---|---|
| TMC278 | 1 | 0.505 | <0.4 | <0.4 | 0.421 | <0.4 | <0.4 | <0.4 |
| TMC278 | 2 | 0.562 | 0.441 | 0.518 | 0.645 | <0.4 | <0.4 | 0.527 |
| TMC278 | 3 | 0.462 | <0.4 | <0.4 | <0.4 | <0.4 | <0.4 | 0.769 |
| TMC278 | 4 | 0.576 | 0.575 | 0.549 | <0.4 | 0.424 | 0.475 | 0.400 |
| compound 1 | 1 | 3.93 | 6.39 | 10.0 | 9.95 | 7.17 | 6.07 | 5.75 |
| compound 1 | 2 | 2.37 | 12.6 | 15.1 | 13.6 | 12.7 | 8.86 | 12.0 |
| compound 1 | 3 | 4.08 | 9.95 | 14.2 | 13.2 | 16.6 | 12.4 | 20.0 |
| compound 1 | 4 | 4.46 | 10.5 | 15.9 | 13.0 | 9.89 | 10.5 | 11.6 |

Example 10

In vivo testing of laser drilled melt extruded tube containing two sets of microparticles Tubes with inner diameter of 4.5 mm were extruded from polydioxanone ($IV_{HFIP}$=1.99 dl/g) using a ¾ inch single screw extruder fitted with a tube die. The dimensions of the tube were monitored using an in-line laser diameter measuring system and maintained using a puller. Following the extrusion the tubes were laser drilled. In preparation for the laser drilling a mask design was prepared that located the holes 260 microns apart from one another. Scanning electron microscopy was used to size the inner and outer diameter of the holes. Results showed that the outer diameter was averaged 100 microns and that of the inner averaged 30 microns. The microparticles were prepared as described in Example 9. Approximately 133 mg of the microparticle mixture was introduced into the tubes.

The prepared tubes were implanted into the subcutaneous space on the back of four male Sprague-Dawley rats weighing between 250-350 grams. The dose of TMC278 was 139 mg/kg and the dose of compound 1 was 64 mg/kg. The tail vein was sampled at pre-determined time points. Blood samples were immediately centrifuged to extract the plasma, and plasma was analyzed for compound 1 and TMC278 by LC/MS/MS. The lower limit of quantitation for TMC278 and compound 1 was 0.4 ng/ml and 2.0 ng/ml, respectively. Values for the tested plasma concentrations at each time point for each drug are tabulated in Table 6.

TABLE 6

TMC278 and compound 1 plasma concentrations

| Analyte | Animal # | 3 hour ng/ml | 1 day ng/ml | 3 day ng/ml | 7 day ng/ml | 14 day ng/ml | 28 day ng/ml | 35 day ng/ml |
|---|---|---|---|---|---|---|---|---|
| TMC278 | 1 | 0.551 | <0.4 | <0.4 | <0.4 | <0.4 | <0.4 | <0.4 |
| TMC278 | 2 | 1.42 | 0.432 | <0.4 | 0.4 | <0.4 | 0.451 | 0.403 |
| TMC278 | 3 | 2.51 | 1.22 | 1.14 | 0.695 | 0.425 | 1.36 | 2.11 |

TABLE 6-continued

TMC278 and compound 1 plasma concentrations

| Analyte | Animal # | 3 hour ng/ml | 1 day ng/ml | 3 day ng/ml | 7 day ng/ml | 14 day ng/ml | 28 day ng/ml | 35 day ng/ml |
|---|---|---|---|---|---|---|---|---|
| TMC278 | 4 | 1.61 | <0.4 | <0.4 | <0.4 | 0.456 | 0.773 | 0.881 |
| compound 1 | 1 | 2.88 | <2 | <2 | <2 | <2 | <2 | <2 |
| compound 1 | 2 | 16.4 | 4.20 | 3.35 | 3.44 | 2.70 | 4.32 | 3.56 |
| compound 1 | 3 | 27.0 | 9.25 | 6.06 | 3.13 | 2.26 | 13.0 | 13.0 |
| compound 1 | 4 | 16.5 | 3.71 | <2 | <2 | 3.66 | 4.30 | 2.57 |

Example 11

In Vivo Testing of Laser Drilled Melt Extruded Tube Containing Two Sets of Microparticles Formulated With F108

The laser drilled melt extruded tube was prepared as described above in example 10. The microparticles were prepared by the spinning disc method using a 3% (w/w) polymer/acetone solution. Two sets of microparticles were prepared. The target composition of one set was 70% (w/w) TMC278, 20% (w/w) PLGA 50/50 (Lakeshore Biomaterials $IV_{HFIP}$=0.79 dl/g), and 10% (w/w) F108 (BASF). The target composition of the other set of microparticles was 70% (w/w) compound 1, 20% (w/w) PLGA 50/50 (Lakeshore Biomaterials $IV_{HFIP}$=0.18 dl/g), and 10% (w/w) F108. The F108 was added to the polymer solution.

The conditions of disc speed and cone inlet and outlet temperatures were the same as those used in examples 9 and 10. The loadings of TMC278 and compound 1 in the microparticles was measured by HPLC, resulting concentrations were 61% (w/w) and 50% (w/w) respectively.

The size range of the microparticles was determined by randomly selecting a sample of microparticles and placing them on the stage of an optical microscope and using a ruler to measure the various sizes of the microparticles in the randomly selected sample. The size range of the TMC278 and compound 1 microparticles was 10-100 microns and 20-100 microns, respectively. Microparticles were mixed as described in example 9. Approximately 133 mg of the microparticle mixture was introduced into tubes using a spatula to transfer the contents.

The prepared tubes were implanted into the subcutaneous space on the back of four male Sprague-Dawley rats weighing between 250-350 grams. The dose of TMC278 and compound 1 was 109 mg/kg and 78 mg/kg, respectively. The tail vein was sampled at pre-determined time points. Blood samples were immediately centrifuged to extract the plasma, plasma was analyzed for compound 1 and TMC278 by LC/MS/MS. The lower limit of quantitation for TMC278 and compound 1 was 0.4 ng/ml and 2 ng/ml, respectively. The results of the tested plasma concentrations for each time point for each drug are tabulated in Table 7.

TABLE 7

TMC278 and compound 1 plasma concentrations

| Drug | Animal # | 3 hour ng/ml | 1 day ng/ml | 3 day ng/ml | 7 day ng/ml | 14 day ng/ml | 28 day ng/ml | 35 day ng/ml |
|---|---|---|---|---|---|---|---|---|
| TMC278 | 1 | 2.12 | 0.797 | 0.485 | <0.4 | 0.6 | 2.13 | 2.17 |
| TMC278 | 2 | 1.40 | 0.522 | <0.4 | <0.4 | <0.4 | 0.539 | 0.744 |
| TMC278 | 3 | 2.42 | 0.939 | 0.521 | 0.405 | 0.478 | 1.13 | 1.48 |
| TMC278 | 4 | 1.02 | <0.4 | <0.4 | <0.4 | 0.664 | 2.19 | 2.48 |
| compound 1 | 1 | 59.1 | 6.13 | 3.36 | <2 | 8.25 | 22.1 | 13.1 |
| compound 1 | 2 | 26.9 | 2.54 | <2 | 2.89 | <2 | 6.03 | 7.25 |
| compound 1 | 3 | 39.2 | 4.36 | <2 | <2 | <2 | 12.3 | 10.7 |
| compound 1 | 4 | 17.3 | 2.98 | <2 | <2 | 6.27 | 16.3 | 15.4 |

We claim:

1. A method of delivering to a human subject one or more drugs that is an anti-HIV drug or an HCV drug comprising subcutaneously administering to the subject
a degradable pharmaceutical implant comprising
a tube that is defined by an outer wall, wherein the outer wall is fabricated from a degradable polymer; has a plurality of openings on its surface; and completely surrounds a cavity,
and wherein the cavity contains at least one set of microparticles embedded in a hydrogel; wherein the at least one set of microparticles comprises the one or more drugs and a biocompatible, biodegradable polymer;
and wherein the size of the microparticles is selected such that the majority of the microparticles cannot pass through the openings.

2. The method of claim 1, wherein the degradable polymer is a copolymer of lactide and glycolide.

3. The method of claim 1, wherein the degradable polymer is a poly(dioxanone).

4. The method of claim 1, wherein the biocompatible, biodegradable polymer is an aliphatic polyester, a poly (amino acid), a copoly(ether-ester), a polyalkylene oxalate, a polyamide, a poly(iminocarbonate), a poly(orthoester), a polyoxaester, a polyamidoester, a polyoxaester containing amine groups, a poly(anhydride), a polyphosphazene, or a blend thereof.

5. The method of claim 1, wherein the biocompatible, biodegradable polymer is a copolymer of lactide and glycolide.

6. The method of claim 1, wherein at least 85% (w/w) of the microparticles are locked in the cavity of the implant.

7. The method of claim 1, wherein the cavity contains one set of microparticles.

8. The method of claim 1, wherein the cavity contains two or more sets of microparticles.

9. The method of claim 1, wherein the cavity contains two sets of microparticles.

10. The method of claim 1, wherein the cavity contains three sets of microparticles.

11. The method of claim 1, wherein the one or more drugs is an anti-HIV drug.

12. The method of claim 1, wherein the one or more drugs is an HCV drug.

13. The method of claim 1, wherein the one or more drugs is a protease inhibitor.

14. The method of claim 1, wherein the one or more drugs is a non-nucleoside reverse transcriptase inhibitor.

15. The method of claim 1, wherein the one or more drugs is a nucleoside reverse transcriptase inhibitor.

16. The method of claim 1, wherein the one or more drugs is a nucleotide reverse transcriptase inhibitor.

17. The method of claim 1, wherein the one or more drugs comprise two nucleoside reverse transcriptase inhibitors and a non-nucleoside reverse transcriptase inhibitor.

18. The method of claim 1, wherein the one or more drugs comprise two nucleoside reverse transcriptase inhibitors and a protease inhibitor.

19. The method of claim 1, wherein the one or more drugs comprises rilpivirine or a pharmaceutically acceptable salt thereof.

* * * * *